United States Patent [19]
Hayakawa et al.
[11] 4,287,768
[45] Sep. 8, 1981

[54] BEAM DEFLECTION METHOD AND APPARATUS FOR SECTOR SCAN ULTRASOUND IMAGING SYSTEMS

[75] Inventors: Yoshihiro Hayakawa; Hiroshi Fukukita, both of Kawasaki, Japan

[73] Assignee: Matsushita Electric Industrial Company, Limited, Osaka, Japan

[21] Appl. No.: 93,019

[22] Filed: Nov. 9, 1979

[30] Foreign Application Priority Data

Nov. 13, 1978 [JP] Japan ............................ 53-140281
Aug. 13, 1979 [JP] Japan ............................ 54-103042

[51] Int. Cl.³ ............................ G01N 29/00
[52] U.S. Cl. ............................ 73/626
[58] Field of Search ............................ 73/626, 628, 641; 367/103, 105, 122, 123, 126, 138

[56] References Cited

U.S. PATENT DOCUMENTS 4,107,685 8/1978 Martin et al. ............................ 367/105
4,224,829 9/1980 Kawabuchi et al. ............................ 73/626

*Primary Examiner*—Stephen A. Kreitman
*Attorney, Agent, or Firm*—Lowe, King, Price & Becker

[57] ABSTRACT

Beam deflection delay time data of (L×M) data bits are stored in a read-only memory from which each datum is retrieved successively when the ultrasound beam is deflected to a given angle and repeatedly accumulated in a digital adder through a latching circuit connected between the output and input of the adder, where L is the number of discrete steps of deflection angle and M is a binary number representing the total delay time of piezoelectric transducers. The successively latched data is distributed to respective programmable counters for presetting the count values thereof to store therein respective delay time data. High frequency count pulses are supplied to the counters after the latter has been preset for delivery of carry outputs to the associated piezoelectric transducers. Beam convergence delay time data is also stored in a second memory from which each datum is retrieved for each transducer element and accumulated so that a tapered configuration of binary differential numbers is created and added to the beam deflection delay time data for converging the ultrasound beam.

17 Claims, 7 Drawing Figures

ULTRASOUND PROBE
10
A0
A1
AN
C0
C1
CN
CTR0
CTR1
CTRN
P0
P1
PN
e0
e1
eN
RING COUNTER
12
LATCHING CIRCUIT
3
DELAY
11
ADDER CIRCUIT
2
4
PROM
1
CTR
5
AND
9
OSC
8
DIVIDE BY "m"
7
DIVIDE BY "n"
6
AND
13
CTR
15
14

TO $CTR_0 \sim CTR_N$
FROM AND 9
3
2
LATCH
3-4
3-3
3-2
3-1
4-BIT ADDER
2-4
2-3
2-2
2-1
H
L
8-BIT PROM
1

ULTRASOUND PROBE
CTR₀
CTR₁
CTRN
RING COUNTER
ADDER
DELAY
LATCHING CIRCUIT
LATCH
OSC
AND
ADDER CIRCUIT
4-BIT ADDER
DIVIDE BY "m"
PROM
CTR
DIVIDE BY "n"

ADDERS
LATCHES
2-1
2-2
2-3
2-4
3-1
3-2
3-3
3-4
ADDER 27
LATCH 25
ADDER 24
LSB
MSB
TO CTR0~CTRN

ULTRASOUND PROBE
10
RECEIVE UNIT
38
$A_0$
$A_1$
$A_N$
$CTR_0$
$CTR_1$
$CTR_N$
RING COUNTER
12
ADDER
27
37
DL
11
4
LATCHING CIRCUIT
3
LATCH
25
35
26
36
ADDER CIRCUIT
2
4-BIT ADDER
24
34
33 SWITCHING NETWORK
33
PROM
1
CTR
5
30
31
32
AND
CTR
21
OSC
8
1/m
6
1/n
7
AND
13
14

BEAM DEFLECTION METHOD AND APPARATUS FOR SECTOR SCAN ULTRASOUND IMAGING SYSTEMS

BACKGROUND OF THE INVENTION

The present invention relates to ultrasound imaging systems of a sector scan type using a linear array of piezoelectric transducers, and in particular to a method and apparatus for scanning the main ultrasound beam of the transmitted acoustic energy based on stored digital information representing the delay time between adjacent transducers.

It is a well known fact that when the piezoelectric elements are activated simultaneously the acoustic energy transmitted therefrom forms a main ultrasound beam whose axis is perpendicular to the linear array and when they are activated successively at different timing the axis of the main beam is deflected at an angle to the perpendicular depending on the amount of the time differential between adjacent transducers.

In a prior art method, the delay times are represented by digital data and stored in a memory from which the data for each of deflection angle of the main beam is retrieved. Therefore, the number of bits to be stored in the memory would amount to L×M×N, where L is the number of discretely varying deflection angles, M is the numbe of bits required to represent the delay time to be introduced to each transducer element, and N, the total number of the transducer elements. Assume that L=100, M=8 and N=32, the total number of bits is 25600 bits, or 3200 bytes. This number represents a substantial amount of storage capacity and a complicated control circuitry would be required if the linear array is activated at a high speed.

To solve this problem Japanese patent application No. 50-135082 laid open to public inspection under publication No. 52-59974 on May 17, 1977, discloses an apparatus in which L×N bits of time delay data are stored in a read-only memory and each set of N bits is transferred to an N-bit shift register in parallel form. The shift register is driven by clock pulses to shift the received data in succession. The parallel outputs of the shift register are thus varied discretely by the amount of "1" bit at the most and applied through parallel gates to respective up-down counters which are associated with respective piezoelectric transducers. The length of period during which each gate is held open depends on the total number of "1" bits successively stored in each bit position of the shift register, so that by supplying through the associated gate each up-down counter is preset to a different count value which represents the time the associated transducer is activated with respect to a reference time. The up-down counters are then driven by high frequency input pulses and deliver carry output pulses successively to the transducers when the preset count values are reached.

However, in the disclosed prior art system the binary differential value or time difference between adjacent transducers is limited to a single bit and since it is desirable to have a binary differential value of more than 1 bit for purposes of achieving a greater angle of deflection, the disclosed system falls short of the ideal.

Furthermore, the memory capacity required for the prior art system is L×N bits which would amount to 3200 bits or 400 bytes on the assumption that L=100 and N=32 which are the typical values of a practical embodiment. This is a substantial amount of memory and reduction of this capacity is desirable for purposes of economy.

SUMMARY OF THE INVENTION

A combined solution to the limitation on the binary differential value and to the requirement of a substantial amount of memory capacity is obtained by repeatedly accumulating a stored delay time data to generate an output data which increases as a function of time and successively presetting programmable drive counters in accordance with said output data in step with each accumulation of the data.

This permits the reduction of the memory capacity to L×M data bits of which the typical value is 800 bits or 100 bytes, where M is the number of bits representing binary number corresponding to a total delay time for each deflection angle. The M data bits are retrieved successively from a memory and repeatedly accumulated in a digital adder circuit through a latching circuit which is connected in a feedback circuit between the output and an input of the adder.

Since the M data bits stored in the memory can represent a substantial range of binary numbers without increasing the total number of memory locations, the accumulated data bits assume a binary differential value of two or more bits when the beam is deflected at a substantial angle with respect to a reference.

Preferably, the adder circuit comprises M+K data bits, where K is a binary number of (N−1) and N is the number of transducer elements, and the M data bits retrieved from the memory are supplied to the lower M-bit positions of the adder circuit. The latching circuit also comprises M+K data bits for latching the accumulated data bits and feeding the latched data to the adder circuit. The higher M data bits of the latching circuit are utilized to preset programmable counters which are connected to respective transducer elements.

According to another feature of the invention, a second memory is provided for storing a set of N data bits for each of the deflection angles. Each data represents an additional amount of delay time to be added to the beam deflection delay time for purposes of converging the ultrasound beam to achieve a sharply defined image. Each bit in the second memory corresponds to a respective one of the transducer elements and is retrieved in synchronism with the beam deflection delay time data and successively added or subtracted in a second digital adder through a second latching circuit in the same manner as the beam deflection data is obtained. The first half of the N data bits are added up successively while the second half is subtracted from the added first half so that the amount of binary differential value increases as a function of the position of the transducer elements until the midpoint is reached and then decreases until the last position is reached, thereby creating a tapered configuration of binary differential values across the transducer elements.

BRIEF DESCRIPTION OF THE DRAWINGS

The invention will be further described by way of example with reference to the accompanying drawings, in which.

DETAILED DESCRIPTION

Before going into the details of the present invention, reference is first made to the principle of the invention. In the sector scan type ultrasound diagnostic system wherein a plurality of piezoelectric transducer elements are arranged on a linear array configuration and successively activated, the unit delay time T between any two successively arranged transducer elements for a given deflection angle $\theta$ of the main beam from the array, is given by the equation $T=d \sin \kappa/C$, where d is the center-to-center spacing between successive transducer elements and C is the velocity of acoustic energy travelling within a subject body. Therefore, the activation of the "n"th transducer element of an N-element linear array is delayed by the length of time which is an integral multiple of the unit delay time with respect to the start of each scan cycle and given by the equation $T_n=(d \sin \theta/C)\times(n-1)$.

It is appreciated therefore that given a deflection angle all the delay times $T_1$ to $T_N$ for the elements No. 1 to No. N can be derived by successively adding up the unit delay time of the given deflection angle. In the present invention, the unit delay time for each deflection angle is binary represented and stored in a digital memory as will be described hereinbelow.

Figure 1:
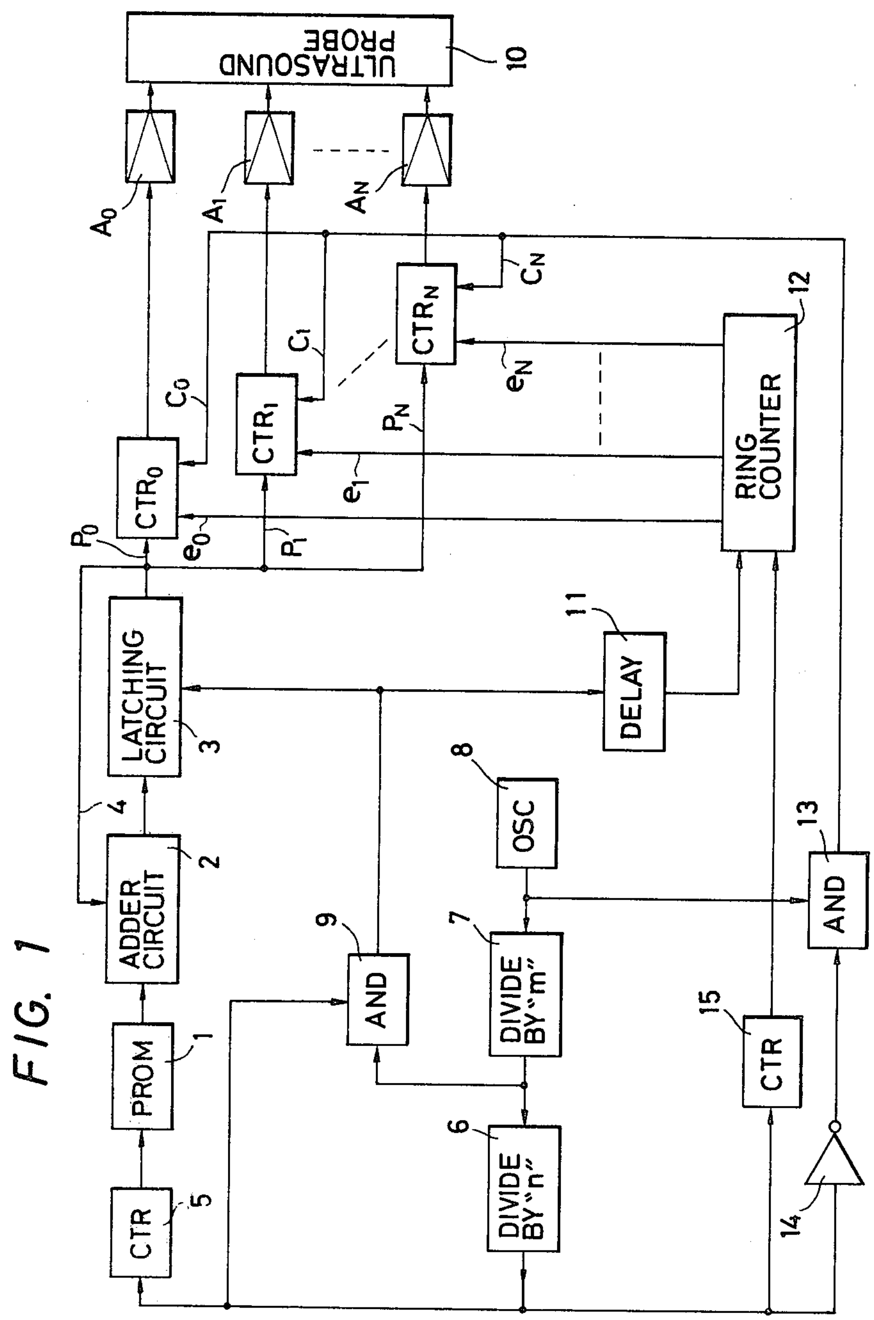
FIG. 1 is a schematic illustration of a first embodiment of the present invention.

Referring now to FIG. 1, a first preferred embodiment of the scanning system of the invention is schematically illustrated. The system comprises a digital memory such as programmable read-only memory 1 which stores a set of delay time data. Each delay time datum represents the total delay times of the transducer elements of an untrasound probe 10 in 8 bits, for example. If the system is assumed to have 100 resolutions or discrete values of deflection angle, there is a set of 100 delay time data stored in the memory 1. Each delay data of 8 bits is successively read out and supplied to an input of an adder circuit 2 whose output is coupled to a latching circuit 3. The output of the latching circuit 3 is connected through a feedback circuit 4 to another input of the adder circuit 2 to provide summation of the two input data. In order to successively read out the delay datum, the memory 1 derives its address signal from the binary output of an address counter 5 which in turn takes its input from a divide by "n" counter 6.

Figure 3:
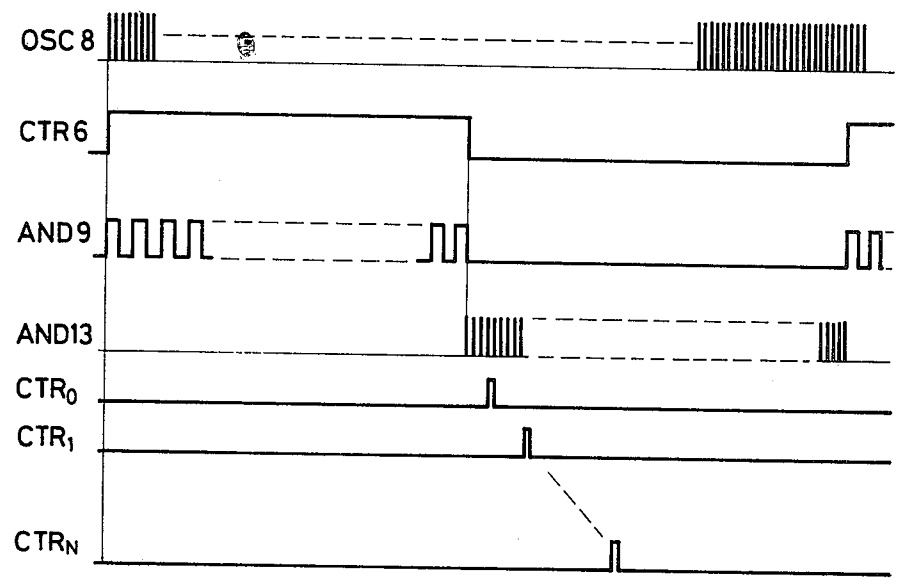
FIG. 3 is an illustration of waveforms associated with the embodiment of FIG. 1.

An oscillator 8 is provided which supplies a train of pulses with a duration of the order of nanoseconds. The oscillator output is supplied to a divide by "m" counter 7 to provide an output at a frequency which is an integral submultiple of the oscillator frequency. The output of the counter 7 is supplied to the divide by "n" counter and also to an AND gate 9. The output frequency of the divide by "n" counter 6 is thus an integral submultiple of the output frequency of the counter 7 and is used as a scan enable pulse (see FIG. 3) which causes the counter 5 to address the memory 1 so that for each one of the 100 discrete steps of deflection the corresponding delay time datum is read out from the memory 1.

In the presence of each scan enable pulse, the AND gate 9 is enabled to pass the output pulses of counter 7 to the enable terminal of the latching circuit 3 as well as to a delay circuit 11. The dividing factors "m" and "n" of the counters 6 and 7 are so selected that the number of pulses generated from the counter 7 during the scan enable pulse is equal to the number of piezoelectric elements contained in the array 10, for example, 32. Therefore, the latching circuit 3 is enabled 32 times during each scan enable pulse and the adder circuit 2 successively adds up the data retrieved from the memory 1 to the feedback data which is the representation of the accumulated unit delay times.

The system includes a plurality of programmable or presettable counters $CTR_0$ to $CTR_N$ (where N is equal to 32 in this illustrative embodiment). The counters $CTR_0$ to $CTR_N$ have their program or preset input terminals $P_0$ to $P_N$ connected together to the binary output of the latching circuit 3 and have their enable terminals $e_0$ to $e_N$ connected respectively to the output terminals of a ring counter 12 which takes its input from the delay circuit 11. Therefore, the programmable counters $CTR_0$ and $CTR_N$ are successively enabled at times which are slightly delayed from the times the latching circuit 3 is enabled so that the counter value of each programmable counter is preset in accordance with a respective one of the successively accumulated delay time data. In this way, all the programmable counters are ready to successively activate the transducer elements of the ultrasound probe 10 through respective amplifying drivers $A_0$ to $A_N$. These preset counters take their input pulses through clock terminals $c_0$ to $c_N$ from the oscillator 8 when AND gate 13 is enabled in response to an inverted output of the divide by "n" counter 6 by means of an inverter 14. Thus, in response to the expiration of the scan enable period, the programmable counters $CTR_0$ to $CTR_N$ are supplied with higher clock rate pulses and successively deliver output pulses at times which are respectively delayed by amounts corresponding to the respectively present delay time data. The ultrasound probe 10 is thus activated to successively send ultrasound pulses into a subject body in order to receive echo signals returning from any interfaces present within the subject body during the receive mode which commences at the end of transmission of the last ultrasound pulse to the leading edge transition of a subsequent scan enable pulse.

In response to the subsequent scan enable pulse from the counter 6, the next delay time data is addressed in the memory 1 and applied to the adder circuit 2. The above process is repeated 100 times to permit the main beam of the probe 10 to deflect through a predetermined angle.

Figure 2:
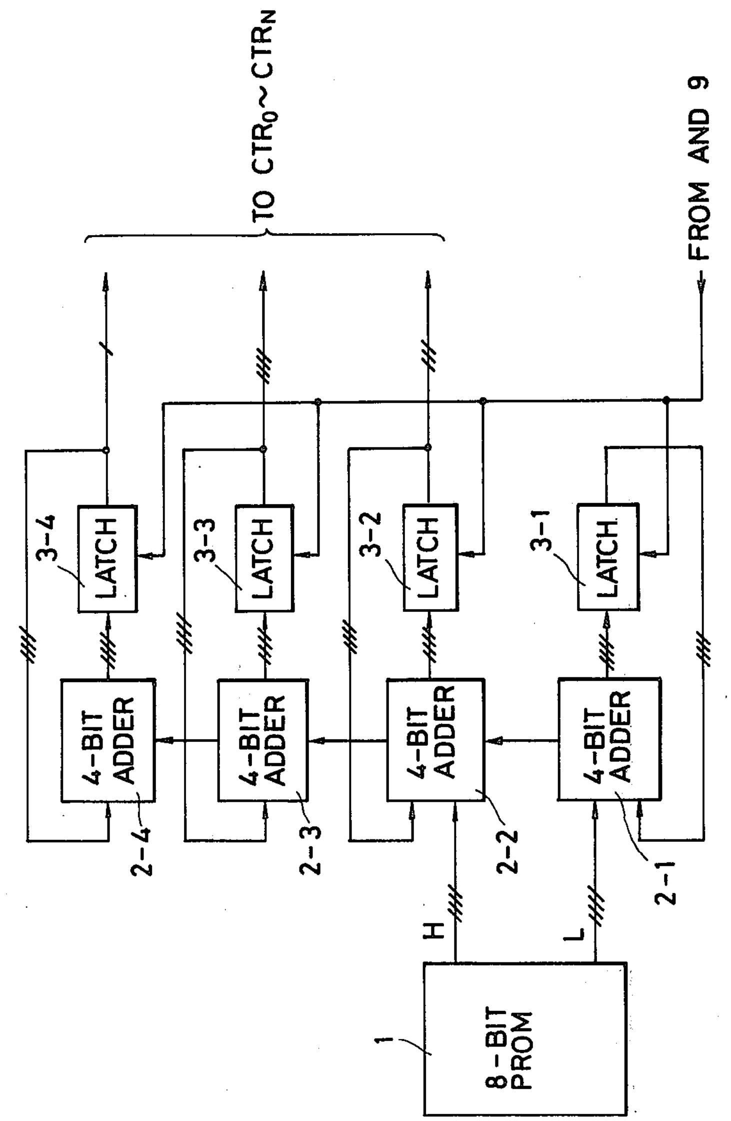
FIG. 2 is an illustration of the details of the adder and latching circuits of FIG. 1.
Figure 4:
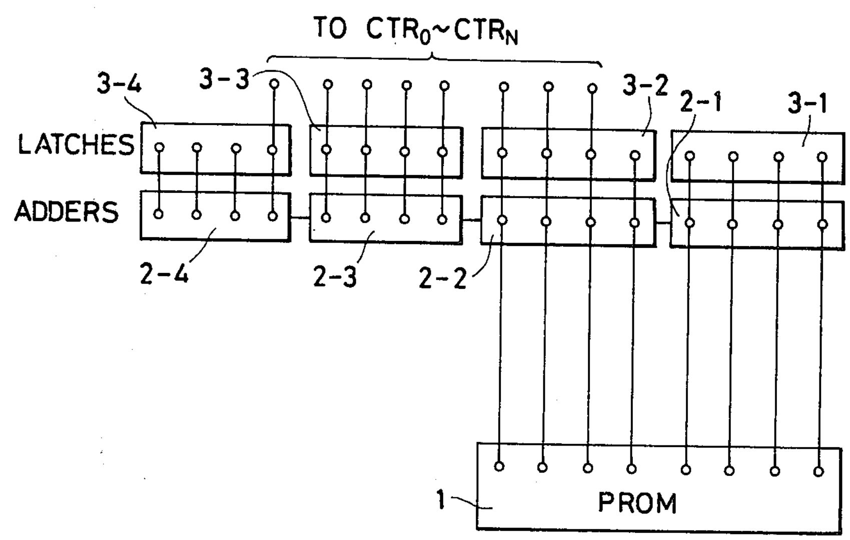
FIG. 4 is an illustration of the interconnection of the circuit of FIG. 2.

In a practical embodiment, the details of the adder circuit 2 and latching circuit 3 are illustrated in FIG. 2. The adder circuit 2 comprises a set of four 4-bit digital adders 2-1, 2-2, 2-3 and 2-4 of the type 74283 available from Texas Instruments which are arranged in the order of lower to higher significant bits so that the carry bit of each lower bit adder is applied to the next higher bit adder. The programmable read-only memory 1 has an 8-bit data format and supplies a lower 4-bit delay time data to the lowest bit adder 2-1 and a higher 4-bit data to the next higher bit adder 2-2. The outputs of the adders 2-1 and 2-2 are respectively connected to latches 3-1 and 3-2 whose outputs are coupled through respective feedback circuits to the associated adders. In like manner, the outputs of the higher bit adders 2-3 and 2-4 are connected respectively to latches 3-3 and 3-4 whose outputs are respectively fed back to the associated adders. The outputs of the latching circuit 3 are connected to the programmable counters $CTR_0$ to $CTR_N$ so that the higher 3 bits of adder 2-2 are transmitted through latch 3-2, the full four bits of adder 2-3 are transmitted through latch 3-3 and a lowest 1 bit of the highest adder 3-4 is transmitted through latch 3-4, as clearly shown in FIG. 4. Therefore, the adder circuit 2 constitutes a 13-bit digital adder, of which the higher 8 bits are utilized.

Therefore, the data accumulating circuit, formed by the adder circuit 2 and latching circuit 3, comprises $M+(N-1)$ data bits where M, in this embodiment, is 8 bits which are supplied to the counters CTR's and N is the number of transducer elements which, in this case, is 6 bits.

The operation of the circuit of FIG. 2 will be best understood by assuming that the center-to-center spacing d is 0.45 mm and the main ultrasound beam is deflected at an angle of 0.4 degrees with respect to the perpendicular to the linear array. This assumption given a delay $T_{32}$ (which equals to total delay time) of approximately 63 nanoseconds. Assume that a minimum discrete delay time unit between successively arranged transducers is quantized into "1" bit in a 30-nanosecond duration, the total number of discrete delay time units for the 0.4-degree deflection is "2" and the latter is represented by a binary number (00000010) and stored in the memory 1. Since this delay time data is repeatedly accumulated in the adder and latching circuits and since only the higher 8 bits of the 13 bits of the latching circuit is utilized, the programmable counters $CTR_0$ to $CTR_8$ are supplied with a program data (00000000), the counters $CTR_9$ to $CTR_{31}$ are supplied with a program data (00000001) and the counter $CTR_{32}$ with a data (00000010). Therefore, there is a minimum delay time unit of 30 nanoseconds between the No. 8 and No. 9 transducer elements and between the No. 31 and No. 32 elements, while there is no delay time among the No. 1 to No. 8 elements and among the No. 9 to No. 31 elements.

At the next deflection angle of 0.8 degrees, the delay time $T_{32}$ is approximately 126 nanoseconds so that it roughly corresponds to four times the minimum delay time unit, and the data stored for this deflection angle is (00000100). The repeated accumulation of this data results in an output data (00000000) for counters $CTR_0$ to $CTR_5$, (00000001) for counters $CTR_6$ to $CTR_{15}$, (00000010) for counters $CTR_{16}$ to $CTR_{22}$, (00000011) for counters $CTR_{23}$ to $CTR_{31}$ and (00000100) for counter $CTR_{32}$. Therefore, the transducer elements No. 6 to No. 15 are activated at a delay time of 30 nanoseconds with respect to the No. 1 to No. 5 elements among which there is no delay time, the transducer elements No. 16 to 22 are activated at a delay time of 60 nanoseconds with respect to the elements No. 1 to No. 5, the elements No. 23 to No. 31 at a delay time of 90 nanoseconds, and finally the element No. 32 is activated at a delay time of 120 nanoseconds with respect to the No. 1 to No. 5 elements.

It will be understood therefore that for deflection angles of 1.2, 1.6 and 1.8 degrees, data (00000110), (00001000) and (00001010) are respectively stored in the memory 1.

At a deflecton angle of 12.4 degrees, the total delay time amounts to 1932 nanoseconds so that there are approximately 64 units of minimum delay time and this number is represented by (01000000). The repeated accumulation of this binary number results in a binary differential value of 2 bits, i.e. the time differential between any two transducer elements is two units of the minimum delay time. Further at a deflection angle of 40 degrees at the end of the 100 deflection steps, the total delay time amounts to 5785 nanoseconds and this gives approximately 193 units of the minimum delay time and this corresponds to a binary number (11000001), resulting in a binary differential value of 6 bits.

It is seen therefore that in the present invention a binary differential value of 2 or more can be easily achieved by the repeated accumulation of the stored delay time data with a memory capacity of not more than 100 bytes ($=L \times M$ data bits).

The number of stored bits in memory 1 and the number of program bits stored in counters $CTR_0$ and $CTR_N$ are, of course, determined by the maximum deflection angle and the quantization time.

In the foregoing description, the main beam of the transducer array 10 is deflected only in one direction. If it is desired to sweep the beam in the opposite direction, this can be achieved by reversing the order in which the programmable counters are successively programmed, and in this case a reversible ring counter is used in the place of the counter 12. A counter 15 is provided for this purpose to count the scan enable pulse to supply the reversible ring counter 12 with a command signal to reverse its order of counting in res ponse to a count value of 100 scan enable pulses, so that after the main beam is swept through an angle of 40 degrees in a given direction the beam is swept in the opposite direction by the same amount of deflection with the result that a total deflection angle of 80 degrees is achieved.

To achieve sharply defined images of the returned acoustic signals, it is desirable that the main ultrasound beam be converged into a narrowly tapered shape. This is achieved by modifying the program data supplied to the programmable counters CTR's in accordance with a set of convergence data stored in a second read-only memory.

If the delay time necessary to achieve the beam convergence is assumed to be quantized on the same digital scale as the aforesaid deflection delay time, the amount of $\pm 1$ bit is considered to be sufficient for modifying the program data stored in the programmable counters CTR's for this purpose. Since the program data is composed of the higher 8 bits of the 13-bit digital adder circuit 2, the convergence delay time data is conveniently composed of 4 bits which are added to the lower 4-bits output of the adder 2-1.

Figure 5:
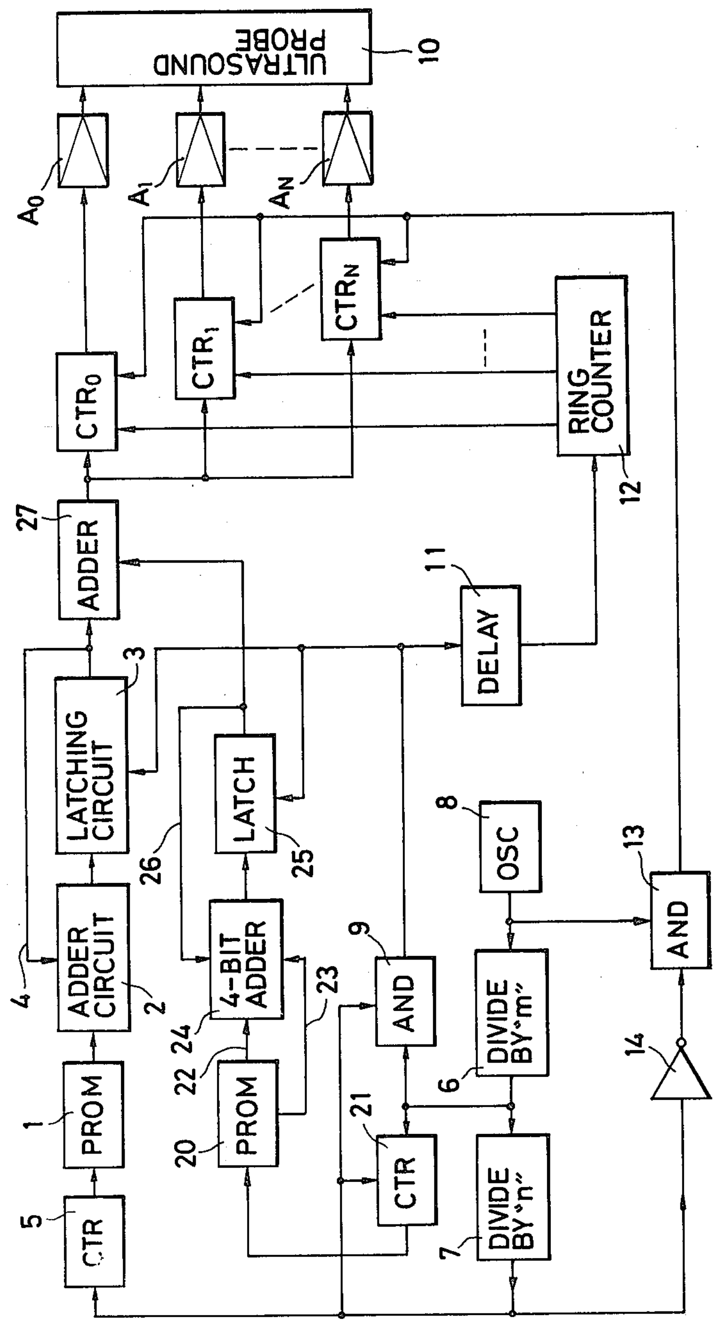
FIG. 5 is a schematic illustration of a second embodiment of the invention.

The embodiment of FIG. 5 incorporates this beam convergence feature in which the same numerals are used to indicate the parts corresponding to the FIG. 1 embodiment. For each angle of deflection, a set of 32 bits is stored in a second programmable read-only memory 20. Further stored in the memory 20 is a sign data including a logical "1" signifying the addition of each bit of the convergence data in a 4-bit digital adder 21 for the first half of the 32 bits and a logical "0" signifying the subtraction of the data for the second half of the 32 bits. The convergence and sign data bits are read out in response to an address signal suppplied from a counter 21 and supplied through lines 22 and 23, respectively, to a 4-bit adder 24. The counter 21 is connected to receive signals from the divider by "m" counter 6 so that each data bit is retrieved in correspondence to each transducer element. The output of the adder 24 is connected to a latch 25 whose output is connected through a feedback path 26 to the adder 24 to accumulate the received data in accordance with the addition or subtraction command signal supplied through the line 23 from the memory 20. Therefore, the data stored in the latch 25 increases in binary number as a function of time until the programmable counter $CTR_{16}$ has been programmed and thereafter decreases as a function of time.

Figure 6:
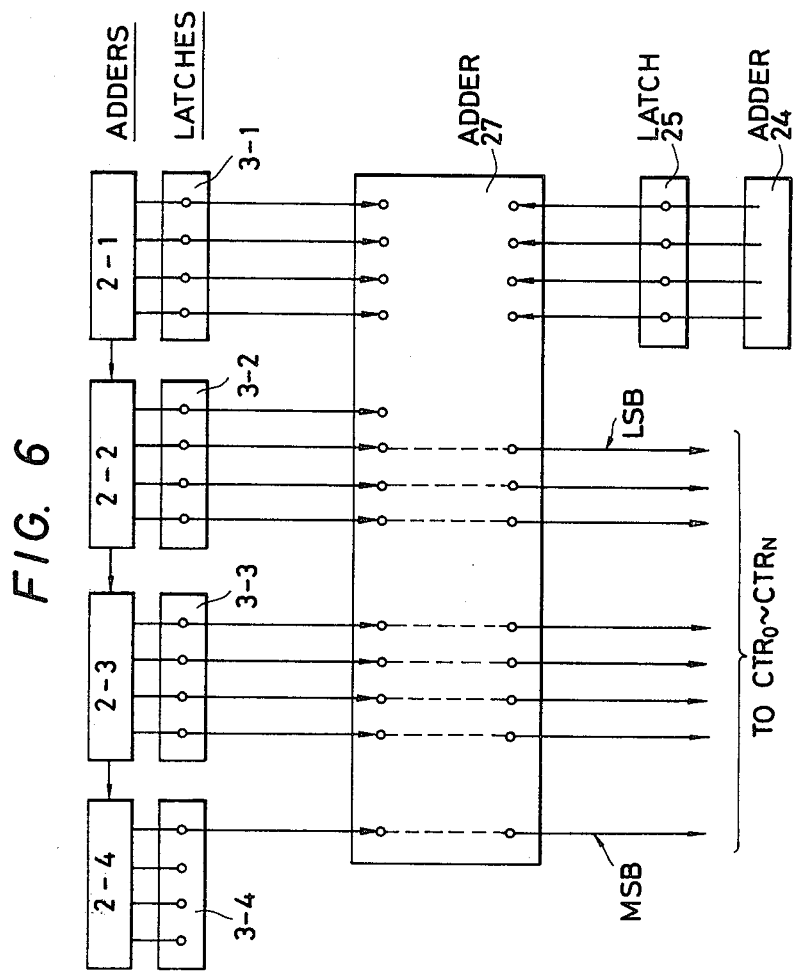
FIG. 6 is an illustration of the details of the adder circuit of FIG. 5 in relation to the associated circuits.

The output data of the latch 25 is further connected to a 13-bit digital adder 27. As shown in detail in FIG. 6, a first group of 13-bit input terminals are connected respectively to the outputs of the latches 3-1 to 3-4 and the lower 4-bit terminals of a second group of 13-bit input terminals are connected to the output terminals of the latch 25. Thus, in the adder 27 the lower four bits of the adders 2-1 and 25 are summed up to modify the higher 8 bits of the 13-bit adder 25 which are connected to the programmable counters $CTR_0$ to $CTR_{32}$.

Figure 7:
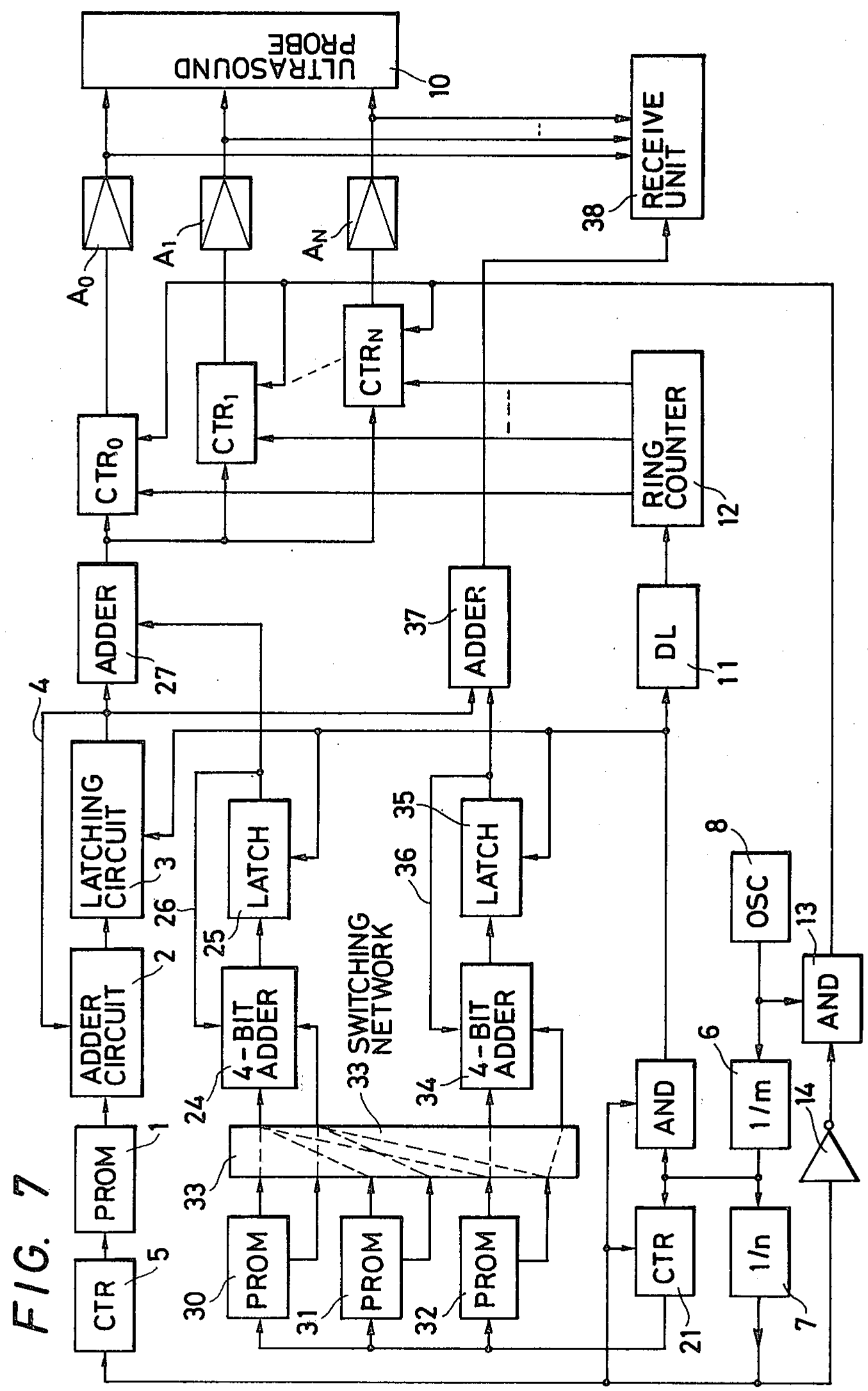
FIG. 7 is an illustration of a modification of the FIG. 5 embodiment.

The beam convergence effect is preferably provided not only with the transmit unit of the diagnostic system, but also with the receive unit by introducing delay times to the received echo signals to achieve a deeper focus range. Although the circuit of FIG. 5 can be simply modified so that the data stored in memory 20 is used both for transmit and receive units, it is desirable that separate data be used for transmission and reception. For this purpose the circuit of FIG. 5 is modified as shown in FIG. 7 in which the same numerals are used to indicate the elements as employed in the circuit of FIG. 5. A set of programmable read-only memories 30, 31 and 32 is provided, each storing a set of different convergence data which are supplied through a switching network 33 to the 4-bit adder 24 and/or another 4-bit adder 34 whose output is fed back through a latch 35 and feedback path 36. The outputs of the latch 35 and the latching circuit 3 are connected to a 13-bit adder 37 of the same construction as adder 27. The switching network 33 is manually resettable to establish desired paths between the memories 30 to 32 and the adders 24, 34. The 13-bit adder 37 feeds its binary output data to the receive unit of 38 of the system which is adapted to accept the return signals through the ultrasound probe 10 and process the signals to form a visual image on a CTR screen.

What is claimed is:

1. A method for successively deflecting an ultrasound beam at different angles to provide a sector scan by successively activating piezoelectric transducer elements, comprising the steps of:

storing a set of delay time data in a memory, each said stored datum being provided for each said deflection angle of said ultrasound beam and representing a binary number corresponding to the delay time between successively activated transducer elements;

retrieving each said delay time data from said memory corresponding to each of said deflection angles;

repeatedly accumulating said retrieved data $(N-1)$ times, where N is the number of said transducer elements, to generate an output data is succession for each said deflection angle; and successively activating said transducer elements in response to said successively generated output data.

2. A method as claimed in claim 1, wherein said stored delay time data is represented by M data bits, and said accumulated data is represented by $(M+K)$ data bits where K is a binary number of $(N-1)$ and said output data is represented by the higher significant M data bits of said accumulated data.

3. A method as claimed in claim 2, wherein said M data bits stored in said memory are a binary representation of the total delay times of said transducer elements.

4. A method as claimed in claim 1, further comprising the steps of:

storing a plurality of sets of data in a second memory, each datum corresponding to each said transducer elements and each set corresponding to each deflection angle of said ultrasound beam, each said datum representing an additional delay time to be added to the first-mentioned delay time for converging said ultrasound beam;

successively retrieving each said datum from said second memory;

repeatedly accumulating the retrieved data for generating an output data in succession; and adding the last-mentioned, successively generated output data to the first-mentioned, successively generated output data.

5. A method as claimed in claim 4, wherein each of said data stored in said second memory comprises a first data representing a time delay and a second data representing the plus or minus sign for adding or subtracting respectively said first data to or from the accumulated first data.

6. Apparatus for successively deflecting an ultrasound beam emanating from an array of piezoelectric transducer elements at different angles in discrete steps by successively activating said transducer elements at delayed timing, comprising:

means for generating low frequency timing pulses timed to correspond to each said deflecting angle of said beam and high frequency timing pulses corresponding in number to said transducer elements to be activated in response to said beam being deflected at each said angle;

a memory in which is stored a plurality of delay time data, each datum representing a binary number corresponding to the delay time between said successively activated transducer elements for each said deflection angle;

means for retrieving each said datum from said memory in response to said low frequency timing pulse;

means for repeatedly accumulating said retrieved data in response to said high frequency timing pulse;

a plurality of counters corresponding to said transducer elements, the count values of said counters being presettable in accordance with an output data from said accumulating means;

means for successively enabling said counters to permit same to be preset to said output data in response to said high frequency timing pulses; and means for supplying count pulses to said counters for successively activating said transducer elements in response to each said preset count values being reached.

7. Apparatus as claimed in claim 6, wherein each said datum is a binary representation of the total delay times of said transducer elements.

8. Apparatus as claimed in claim 6, wherein each said datum is a binary representation of (d sin $\theta/C) \times (N-1/Q)$, where d is the center-to-center spacing between successive ones of said transducer elements, $\theta$ is said angle of deflection, C, the velocity of acoustic energy propagating through a body under investigation, N, the number of said transducer elements, and Q, a unit delay time.

9. Apparatus as claimed in claim 8, wherein said unit delay time is a minimum delay time between said successively activated transducer elements.

10. Apparatus as claimed in claim 8, wherein said unit delay time is a unit quantization time required to generate a single data bit.

11. Apparatus as claimed in claim 6, wherein said repeatedly accumulating means comprises a digital adder having first input terminals connected to receive said retrieved differential time data and second input terminals, and a latch connected to receive an output data from said adder for latching the received data and applying said latched data to said second input terminals of said adder in response to said high frequency timing pulse, the data output of said latch being connected to the preset input terminals of each of said counters.

12. Apparatus as claimed in claim 8, wherein each of said delay time datum is represented by M data bits and wherein said accumulating means comprises $(M+K)$ data bits where K is a binary number of $(N-1)$, the data bits delivered from said accumulating means to said counters being the higher M data bits thereof.

13. Apparatus as claimed in claim 6 or 12, further comprising a second memory in which is stored plural sets of beam convergence data bits, said data bits corresponding in number of said transducer elements and each set corresponding to each deflection angle of said beam, each of said convergence data bit representing an additional delay time for converging said ultrasound beam, said second memory further storing plus and minus sign data bits, means for retrieving each of said data bits and one of said sign data bits from said second memory in response to said high frequency timing pulse, means for repeatedly adding said retrieved convergence data bit from said second memory in response to said high frequency timing pulses in the presence of said retrieved plus sign data bit or repeatedly subtracting the retrieved convergence data bit from the added data bits in response to said high frequency timing pulses in the presence of the retrieved minus sign data bit, and means for adding an output data from said adding-and-subtracting means to the output data from said accumulating means.

14. Apparatus as claimed in claim 13, adapted for use in an ultrasound probe system including beam transmit and receive units, wherein second memory comprises a plurality of memory sections each storing plural sets of beam convergence data bits and plus and minus sign data bits, means for selectively connecting the stored data in said memory sections to said adding-and-subtracting means and to second adding-and-subtracting means constructed identically to the first-mentioned adding-and-subtracting means, and second adding means for adding an output data from said second adding-and-subtracting means to the output data from said accumulating means for providing a combined output data to the receive unit of said system.

15. Apparatus as claimed in claim 13, wherein said adding-and-subtracting means comprises a digital adder having a first set of input terminals connected to said memory, a second set of input terminals and a sign input terminal for permitting said digital adder to act as an adder or a subtractor depending on said sign data bits applied thereto from said second memory, and a latch receptive of an output data from said digital adder for applying the latched data to said second set of input terminals of said adder, an output data from said latch being the output data of said adding-and-subtracting means.

16. Apparatus as claimed in claim 13, further comprising a second memory in which is stored plural sets of beam convergence data bits, said data bits corresponding in number to said transducer elements and each set corresponding to each deflection angle of said beam, each of said convergence data bit representing an additional differential time for converging said ultrasound beam, said second memory further storing plus and minus sign data bits, means for retrieving each of said data bit and one of said sign data bits from said second memory in response to said high frequency timing pulse, means for repeatedly adding said retrieved convergence data bit from said second memory in response to said high frequency timing pulses in the presence of said retrieved plus sign data bit or repeatedly subtracting the retrieved convergence data bit from the added data bits in response to said high frequency timing pulses in the presence of the retrieved minus sign data bit, and means for adding an output data from said adding-and-subtracting means to the output data from said accumulating means, wherein the last-mentioned adding means is identically constructed to said accumulating means and wherein the output data from said adding-and-subtracting means is added to the $N-1)$ data bits of said last-mentioned adding means.

17. Apparatus as claimed in claim 16, wherein said adding-and-subtracting means comprises a digital adder having a first set of input terminals connected to said second memory, a second set of input terminals and a sign input terminal for permitting said digital adder to act as an adder or a subtractor depending on said sign data bits applied thereto from said second memory, and a latch receptive of an output data from said digital adder for applying the latched data to said second set of input terminals of said adder, an output data from said latch being the output data of said adding-and-subtracting means.

* * * * *